United States Patent [19]

Pluim et al.

[11] Patent Number: 5,464,514
[45] Date of Patent: Nov. 7, 1995

[54] METHOD FOR SEPARATING ORGANIC SUBSTANCES

[75] Inventors: Henk Pluim; Jan G. Kraaijenbrink, both of Weesp, Netherlands

[73] Assignee: Duphar International Research B.V., Weesp, Netherlands

[21] Appl. No.: 190,563

[22] Filed: Feb. 2, 1994

Related U.S. Application Data

[63] Continuation of Ser. No. 968,268, Oct. 30, 1992, abandoned, which is a continuation of Ser. No. 703,098, May 22, 1991, abandoned.

[30] Foreign Application Priority Data

May 25, 1990 [EP] European Pat. Off. .............. 90201337

[51] Int. Cl.$^6$ .............................. B01D 61/48; B01D 61/44
[52] U.S. Cl. ................... 204/182.4; 204/182.6; 127/42; 127/46.2
[58] Field of Search .......................... 204/138, 182.4, 204/182.6; 127/42, 46.2

[56] References Cited

U.S. PATENT DOCUMENTS

| | | | |
|---|---|---|---|
| 2,854,393 | 9/1958 | Kollsman | 204/182.5 |
| 3,383,245 | 5/1968 | Scallet et al. | 127/46.2 |
| 3,686,089 | 8/1972 | Korngold et al. | 204/182.4 |
| 4,299,677 | 11/1981 | Venkatsabramanian | 204/182.6 |
| 4,396,477 | 8/1983 | Jain | 204/182.5 |
| 4,463,093 | 7/1984 | Horwath et al. | 435/94 |
| 4,467,033 | 8/1984 | Horwath et al. | 435/105 |
| 4,781,809 | 11/1988 | Falcone, Jr. | 204/182.4 |
| 4,787,940 | 11/1988 | Kayane et al. | 204/182.4 |

FOREIGN PATENT DOCUMENTS

| | | |
|---|---|---|
| 3238280 | 4/1984 | Germany . |
| 0116390 | 9/1979 | Japan . |
| 2014188 | 8/1979 | United Kingdom . |
| 90/15659 | 12/1990 | WIPO . |

OTHER PUBLICATIONS

*Reports of the Asahi Glass Foundation for Industrial Technology*, vol. 54, 1989, pp. 167–174, Yoshihiro Shigemasa and Hiroyuki Saimoto, "Desalting and Separation of Mixed Carbohydrates by Electrodialysis with Ion–Exchange Membranes".

*Chemical Abstracts*, vol. 81, 1974, No. 176902g, Yukio Mizutani et al., "Electrodialysis which separates anions small in electric valency selectively".

*Chemical Abstracts*, vol. 79, 1973, No. 45371u, Hiroshi Shimizu et al., "Problems on the design of a plant for the removal of toxic substances".

*Chemical Abstracts*, vol. 113, 1990, No. 96161d, Chuanhuai Wang et al., "Electrical dialysis technology and apparatus for extracting lactic acid from fermentation fluid".

*Chemical Abstracts*, vol. 112, 1990, No. 181765c, Yoshihiro Shigemasa et al., "Desalting and separation of mixed carbohydrates by electrodialysis with ion–exchange membranes".

*Chemical Abstracts*, vol. 91, 1979, abstract No. 91:125232n, Jean Claude Giorgi, "Purification of sugar syrup by electrodialysis" no month.

*Chemical Abstracts*, vol. 74, No. 19, 10 May 1971, p. 363 col. 2, Abstract No. 98265r, Cenci et al.

*Primary Examiner*—John Niebling
*Assistant Examiner*—Arun S. Phasge
*Attorney, Agent, or Firm*—Stevens, Davis, Miller & Mosher

[57] ABSTRACT

The present invention is concerned with the separation of organic compounds in a mixture using their tendency of binding a weak acid by applying electrodialysis to a mixture of at least one of said organic compounds and said weak acid, while preferably an ionexchange resin is present in the electrodialysis cell.

8 Claims, 1 Drawing Sheet

METHOD FOR SEPARATING ORGANIC SUBSTANCES

This application is a Continuation of application Ser. No. 07/968,268, filed Oct. 30, 1992, abandoned; which in turn is a Continuation of application Ser. No. 07/703,098, filed May 22, 1991, abandoned.

The present invention is concerned with a novel method for the separation of at least one organic substance from a mixture.

The separation of at least one organic substance from a mixture can be established making use of the property of this substance to form a (preferably reversible) complex with a weak acid. Different organic substances form complexes of differential strength with a weak acid. These complexes therefore will have differential electrostatic and/or electrodynamic properties. A separation method for organic substances can be based on isolation of these complexes from a mixture using ion-exchange chromatographic separation, as described in U.S. Pat. No. 2,818,851. There a solution of the mixture containing polyhydroxy substances complexed with borate ion is applied to a column containing a basic ion exchanger. Subsequently, the complexes of the organic substances are eluted from the column using a suitable eluent.

According to the present invention organic substances can be separated by way of an entirely different method, called electrodialysis.

Separation of a mixture by electrodialysis is based on the movement of ions across one or more ion-selective membranes under the influence of a direct electric current. The membranes used for this purpose can be either cation-selective membranes, or anion-selective membranes, whereas optionally also use can be made of bipolar membranes (through which basically only protons and hydroxyl ions can move). Depending on the specific application, an electrodialysis cell can be composed of a cathode compartment and an anode compartment, and an optional number of intermediate compartments, separated by said ion-selective membranes. Herein the, optionally reinforced, ion-selective membranes are spaced apart, generally by gaskets which form liquid compartments.

A number of these cells can be combined to form an array, a so-called electrodialysis stack.

In a typical electrodialysis cell useful for the separation according to the present invention two electrode compartments are separated by compartments containing the mixture to be separated (diluate) and the effluent solution (concentrate), respectively. These compartments are separated from each other and from the electrode compartments by said ion-selective membranes.

In order to avoid stagnant layers in the cell compartments to occur, the respective solutions can be circulated through an external reservoir.

In an electrodialysis stack e.g. up to several hundreds of diluate and concentrate compartments can be placed alternately between the electrode compartments, and the solute flows through the multiple diluate compartments and the concentrate compartments, respectively, can be combined.

In a preferred embodiment of the present invention the separation is carried out in an electrodialysis cell or stack wherein at least one of the compartments between the electrode compartments contains a macro-molecular charged material, such as a poly-electroyte, or an ion-exchange resin (either an anion-exchange resin, or a cation-exchange resin, or a mixed bed resin). The present invention also provides for an electrodialysis apparatus containing an ion-exchange resin as described above.

The weak acid to be used according to the present invention should be a weak acid which is capable of reversibly forming a complex with the organic substance or substances to be separated.

Suitable weak acids for use in the present invention are, for example, inorganic weak acids, like: boric acid, germanic acid, silicic acid, aluminates, plumbates and stannates.

The separation of the organic substances according to the present invention will proceed most efficiently under conditions where there are differences between the various substances in their formation of charged complexes with the weak acid.

The compositions of the solutions in the cell compartments can be varied in order to enhance the separation of the various organic substances. For example, the pH can be varied in order to fine-tune the binding of the weak acid to the organic substances.

The present method is particularly suited for the separation of polar organic substances. More in particular, this method can be applied to the separation of polyols, such as sugars. Examples of sugars which can be separated are 1,2-diols (such as mannite, glucose, fructose, maltulose), and 1,3-diols (such as 2,2-dimethyl-1,3-hexanediol). Also, the separation can be applied to sugar fractions or sugar mixtures obtained e.g. in the course of the production of lactulose from lactose or the conversion of glucose to fructose.

The present separation method can serve several purposes.

One application of this invention is in the separation of a mixture of organic substances, such as a mixture of sugars. In particular, this method is applicable following chemical processes wherein the reaction product contains both starting substances and conversion products which differentially bind to a weak acid. The method is also applicable where the reaction product contains a mixture of products with differential binding strengths towards a weak acid.

In another embodiment the invention is applied to the removal of a contaminating weak acid in a mixture with an organic substance such that part of the organic substance forms a complex with the weak acid. This removal is established by separating the acid-complexed organic substance from the uncomplexed organic substance.

Figure 1:
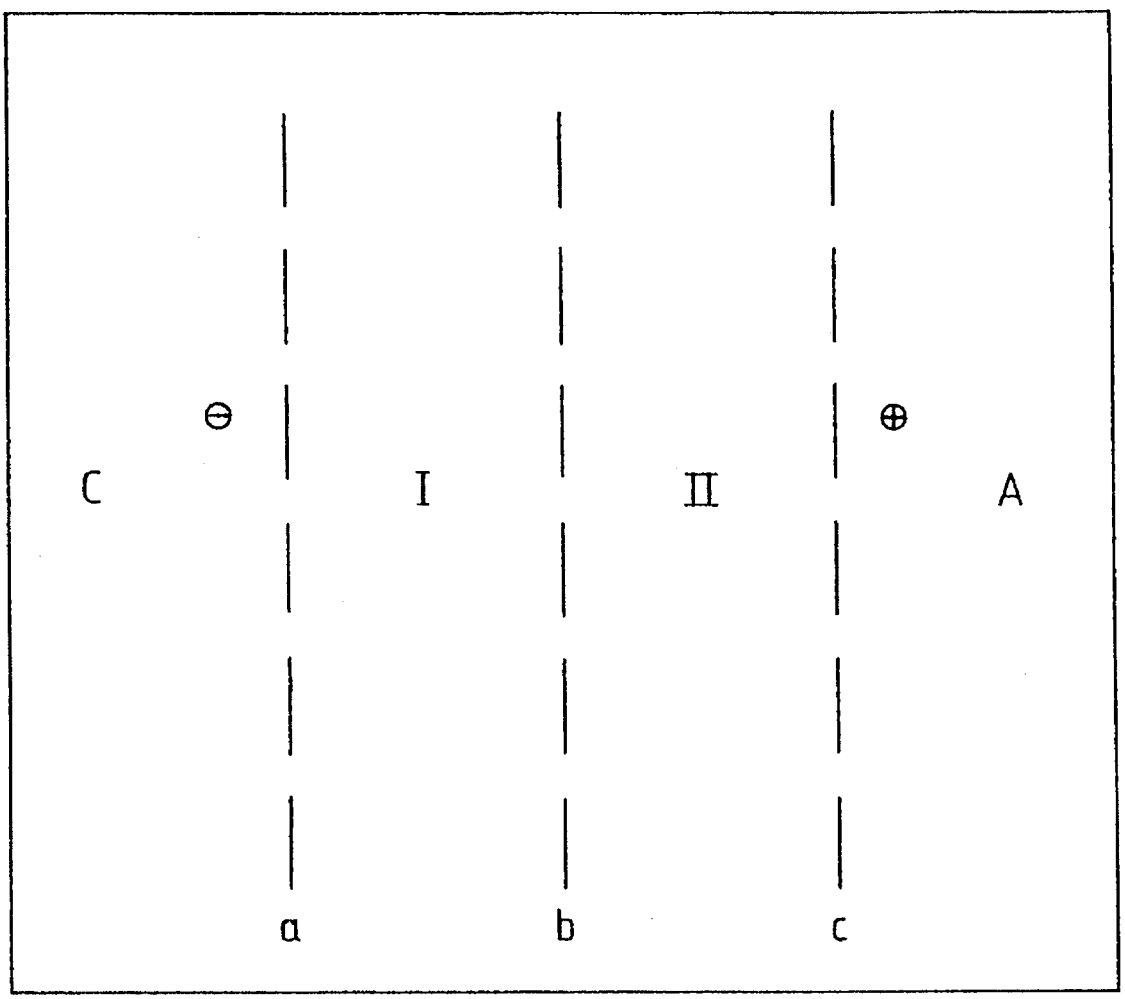
FIG. 1 is a schematic electrodialysis equipment used in the invention.

The present invention is illustrated by the following examples.

EXAMPLE 1

Separation of lactulose and lactose using electrodialysis

Lactulose and lactose are separated in an electrodialysis equipment, consisting of a three-compartment system (BEL-2 from Berghof).

The middle compartment was filled with the weakly basic ion-exchange material MP 62 from Bayer. The cathode compartment was filled with 0.1 mol/l NaOH and the anode compartment was filled with 0.1 mol/l $Na_2SO_4$. The cathode compartment was separated from the inner compartment by a cation membrane, whereas the anode compartment was separated from the inner compartment by an anion membrane.

A mixture of lactose, lactulose and boric acid is led through the inner compartment.

The voltage-current relationship as a function of time was monitored and is represented in the accompanying TABLE I.

TABLE I

Current-voltage profile during electrodialytic separation of lactose and lactulose

| t (min) | 30 | 45 | 60 | 75 | 90 | 105 | 120 | 160 | 180 | 210 | 240 | 270 |
|---|---|---|---|---|---|---|---|---|---|---|---|---|
| I | 0.88 | 0.83 | 0.76 | 0.67 | 0.58 | 0.52 | 0.50 | 0.26 | 0.20 | 0.21 | 0.21 | 0.19 |
| V | 49.8 | 49.8 | 49.8 | 49.8 | 49.8 | 49.8 | 49.8 | 49.8 | 49.8 | 49.8 | 49.8 | 49.8 |

At the start of the experiment the ratio of lactose to lactulose in the middle compartment was 1:1, by weight.

After electrodialysis during 4.5 hours the ratio by weight of lactose to lactulose was 3:1 in the diluate and 1:1.5 in the concentrate.

The separation can be further improved by repeated electrodialysis of the resulting solution.

EXAMPLE 2

Removal of boric acid using electrodialysis

For the separation of boric acid as a complex with an organic substance use can be made of the electrodialysis equipment described in EXAMPLE I.

In an experiment to show the feasability of this method the starting solution in the inner compartment contained 0.59 g boric acid per ml and 4,26 g disaccharide per 100 ml.

After 15 hours of electrodialysis the amount of boric acid in the solution was less than 100 ppm (not detectable by HPLC).

EXAMPLE 3

Separation of lactulose and lactose at different pH values

A mixture of lactose and lactulose was passed through the electrodialysis equipment schematically represented in FIG. 1. The flow rate of the mixture was 1.4–1.8 l/min.

In compartment I the solution to be separated was circulated, whereas the component to be concentrated was collected in compartment II. The compartments A and C are the anode and cathode compartments, respectively (electrode compartments).

The compartments I and II were separated by an anion exchange membrane (type Nepton, Serva); the membranes between compartments C and I and between A and II, respectively, were of the cation exchange type (type Nafion, Berghof).

In these experiments a basic ion exchange resin (MP62) was filled either in compartment I alone, or in both compartments I and II.

The starting conditions in the various experiments are summarized in TABLE II. The concentrations for Compartment I are given in g/100 ml.

TABLE II

| | Compartment | | |
|---|---|---|---|
| | I | II | electrodes |
| Experiment III.1 | 7.7 g lactose<br>7.6 g lactulose<br>3.0 g boric acid<br>pH 9.35<br>MP62 resin | 0.1 mol/l<br>Na$_2$SO$_4$<br><br>pH 6.47 | 0.1 mol/l<br>Na$_2$SO$_4$<br><br>pH 6.47 |
| Experiment III.2 | 6.8 g lactose<br>7.1 g lactulose<br>2.3 g boric acid<br>pH 4.03<br>MP62 resin | 0.1 mol/l<br>Na$_2$SO$_4$<br><br>pH 6.09 | 0.1 mol/l<br>Na$_2$SO$_4$<br><br>pH 6.09 |
| Experiment III.3 | 7.3 g lactose<br>7.1 g lactulose<br>2.3 g boric acid<br>pH 9.27<br>MP62 resin | H$_2$O dist.<br><br>pH 6.6<br>MP62 | 0.1 mol/l<br>Na$_2$SO$_4$<br><br>pH 8.39 |
| Experiment III.4 | 7.0 g lactose<br>6.5 g lactulose<br>2.1 g boric acid<br>pH 4.3<br>MP62 resin | H$_2$O dist.<br><br>pH 6.6<br>MP62 | 0.1 mol/l<br>Na$_2$SO$_4$<br><br>pH 1.1 |

A variable voltage was applied between the anode and the cathode compartments. The current was kept constant at 1.11 A.

The results of the separations in the four experiments are shown in TABLE III.

TABLE III

| | | transfer rate (%) (by weight) | | |
|---|---|---|---|---|
| Experiment | Time (hours) | lactose | lactulose | boric acid |
| 3.1 | 4 | 18.0 | 34.5 | 51.3 |
| | 6 | 24.2 | 88.7 | 86.3 |
| 3.2 | 4 | 8.4 | 69.0 | 34.8 |
| | 6 | 15.1 | 100 | 58.5 |
| 3.3 | 4 | 16.2 | 24.2 | 42.0 |
| | 11 | 23 | 100 | 100 |
| 3.4 | 4 | 9.5 | 35.0 | 27.6 |

EXAMPLE 4

Separation of glucose and fructose.

A mixture of glucose and fructose was applied to electrolysis as described in EXAMPLE 3.

The starting conditions are described in TABLE IV. The concentrations for Compartment I are given in g/100 ml.

TABLE IV

| Experiment | Compartment I | II | electrodes |
|---|---|---|---|
| 4.1 | 3.5 g glucose<br>3.6 g fructose<br>2.5 g boric acid<br>pH 9.18 | $H_2O$ dist.<br><br><br>pH 5.72 | 0.1 mol/l $H_2SO_4$<br><br><br>pH 1.00 |
| 4.2 | 3.5 g glucose<br>3.6 g fructose<br>2.5 g boric acid<br>pH 9.13<br>MP 62 resin | $H_2O$ dist.<br><br><br>pH 5.98 | 0.1 mol/l $H_2SO_4$<br><br><br>pH 1.13 |

The results of the two separation experiments are shown in TABLE V.

TABLE V

| Experiment | Time (hours) | Transfer rate (%) (by weight) | | |
|---|---|---|---|---|
| | | glucose | fructose | boric acid |
| 4.1 | 4 | 53.5 | 67.0 | 65.6 |
| | 6 | 72.5 | 86.8 | 89.5 |
| 4.2 | 4 | 67.1 | 79.8 | 80.4 |
| | 5.5 | 76.9 | 92.3 | 94.0 |

We claim:

1. Method for separation of at least one sugar from a mixture of two or more organic substances, of which at least two are sugars, in an initial concentration ratio, which mixture also contains a weak acid capable of reversibly forming a complex with at least one of the organic substances in the mixture, employing an electrodialysis equipment consisting of at least two electrode compartments wherein electrodes are placed and which are separated by at least one main compartment, said at least one main compartment having an inlet and an outlet, wherein said electrode compartments and said main compartments are separated by ion selective membranes, and wherein an electric potential difference is maintained between the electrodes comprising reversibly forming a complex of the weak acid and at least one of the organic substances in the mixture, leading said mixture into the inlet of said main compartment, and conducting electrodialysis on said mixture in the presence of a macromolecular charged substance, withdrawing the altered mixture from the outlet of said main compartment and leading the mixture back into said inlet until the mixture contains said at least one sugar in a ratio different from the initial concentration ratio.

2. Method according to claim 1, wherein the electrodialysis takes place in the presence of a basic, acid or mixed-bed ion exchanger.

3. Method according to claim 1 wherein the weak acid is selected from the group consisting of boric acid, germanic acid, silicic acid, plumbates, stannates and aluminates.

4. Method according to claims 1 wherein two or more organic substances having differential complexing strengths with said weak acid are separated from each other.

5. Method for the separation of a sugar from a weak acid capable of reversibly forming a complex with said sugar both present in a mixture, employing an electrodialysis equipment consisting of at least two electrode compartments wherein the electrodes are placed, separated by at least one main compartment, wherein said electrode compartments and said main compartments are separated by ion-selective membranes, and wherein all electrode potential difference is maintained between the electrodes, comprising leading said mixture into the inlet of said main compartment, withdrawing the altered mixture from the outlet of said main compartment and leading this back into the inlet of the same or another main compartment until the sugar is substantially free of the weak acid, wherein the electrodialysis takes place in the presence of a macromolecular charged substance.

6. Method according to claim 5, wherein the electrodialysis takes place in the presence of a basic, acid or mixed-bed ion exchanger.

7. Method according to claim 5, wherein the weak acid is selected from the group consisting of boric acid, germanic acid, silicic acid, plumbates, stannates and aluminates.

8. Method according to claim 5, wherein two or more organic substances having differential complexing strengths with said weak acid are separated from each other.

* * * * *